United States Patent [19]
Giese

[11] 3,946,193
[45] Mar. 23, 1976

[54] HEATED INNER SOLE AND BATTERY CASE FOR USE IN BOOT CONSTRUCTION
[76] Inventor: Erik O. Giese, 150 Ocean Lane Drive, Key Biscayne, Fla. 33149
[22] Filed: Aug. 5, 1974
[21] Appl. No.: 494,826

Related U.S. Application Data
[62] Division of Ser. No. 416,209, Nov. 15, 1973, Pat. No. 3,859,496.

[52] U.S. Cl. .................. 219/211; 36/2.6; 36/44; 128/383; 219/528; 219/536
[51] Int. Cl.² ............................................. H05B 1/00
[58] Field of Search .......... 219/211, 523, 528, 529, 219/536; 128/383; 36/2.6, 43, 44

[56] References Cited
UNITED STATES PATENTS

| | | | |
|---|---|---|---|
| 721,270 | 2/1903 | Zeckendorf | 36/2.6 X |
| 974,220 | 11/1910 | West | 128/383 |
| 1,430,404 | 9/1922 | Radford | 219/211 UX |
| 2,692,326 | 10/1954 | Crowell | 219/211 |
| 3,071,877 | 1/1963 | Stickles | 36/44 |
| 3,103,219 | 9/1963 | Chadner | 219/528 X |
| 3,547,725 | 12/1970 | Shomphe et al. | 219/528 X |
| 3,621,191 | 11/1971 | Cornwell | 219/211 |

*Primary Examiner*—C. L. Albritton
*Attorney, Agent, or Firm*—Pennie & Edmonds

[57] ABSTRACT

A heated inner sole for use in a boot where the inner sole comprises a cellular plastic material overlaid by a fabric material having heating elements therebetween. The opposite side of the cellular material has a pressure sensitive adhesive thereon by which the inner sole may be affixed to the inside of a boot. The heating elements are connected by wiring to a battery contained in a battery case carried by slide means attached to the boot heel.

3 Claims, 7 Drawing Figures

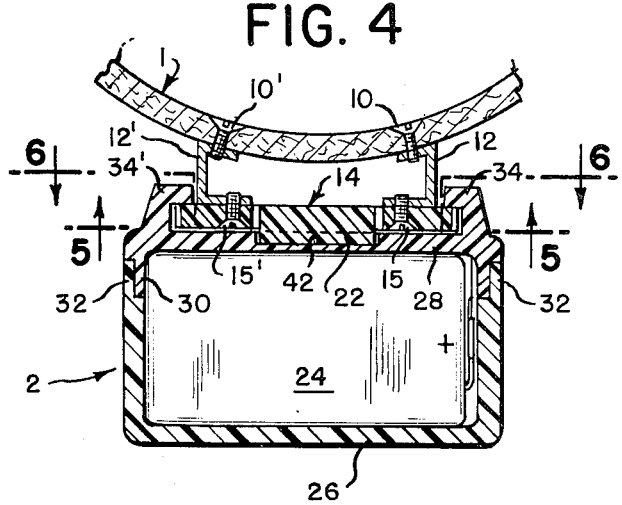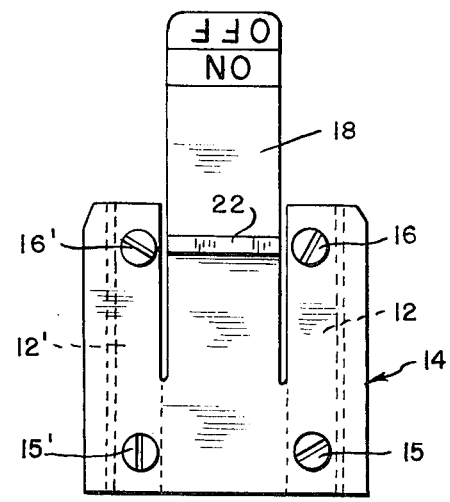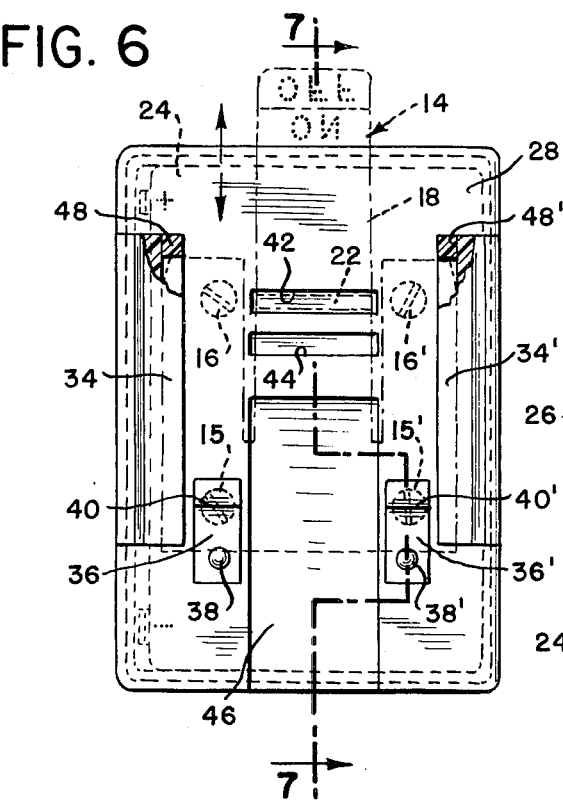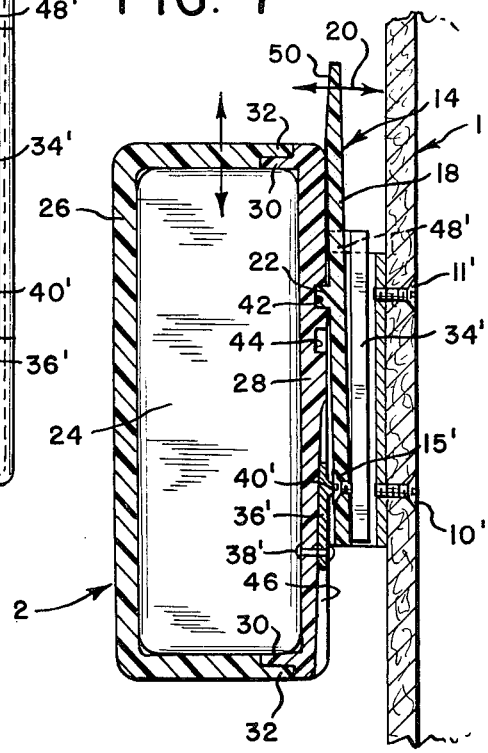

HEATED INNER SOLE AND BATTERY CASE FOR USE IN BOOT CONSTRUCTION

This is a division of application Ser. No. 416,209 filed Nov. 15, 1973, now U.S. Pat. No. 3,859,496.

BACKGROUND OF THE INVENTION

There have been numerous constructions proposed for electrically heating boots or inner soles for use in boots in order that the wearer's feet may remain warm in low temperature conditions. Examples of such constructions are illustrated in a number of patents including U.S. Pat. Nos. 1,274,451, 1,430,404, 2,028,347, 2,692,326 and 3,621,191. None of the constructions of which I am aware however provide a means for conveniently attaching a battery to a boot where the means contains a switch by which the battery may be conveniently switched on and off in order to provide current to electrical resistance wires contained within an inner sole of the boot and where the switch may be operated notwithstanding snow or ice conditions.

Further much of the prior art has required considerable alteration to the boot structure or has required a particular special boot construction. In many instances, such as with ski boots, there are many different types of boots available and usually the wearer is accustomed and desires a particular type of boot. Thus it is desirable that any heated inner sole means for use with boots, and particularly ski boots, be easily adaptable for use in a boot without any major alteration of the boot structure.

An object of my invention is to provide an inner sole which may fit into any boot and which may be connected by wiring to a battery carrying in turn adapted to be attached to the heel portion of the boot.

GENERAL SUMMARY OF THE INVENTION

Broadly my invention comprises a plastic foam inner sole having heating elements thereon which are overlaid by a further fabric layer. The side of the inner sole opposite the heating elements has thereon a pressure sensitive adhesive such that the inner sole may be easily secured within a boot. A movable slide means is mounted in the exterior heel portion of the boot and includes means for engaging a case which may slide up and down on the slide means. The casing contains a battery and has thereon contact means adapted to engage contacts contained on the slide and which in turn are attached to wiring leading to the inner sole. Latch means are contained on the slide means for locking the case against movement and into positions where the contacts on the case connect or disconnect with the contacts on the slides.

DESCRIPTION OF THE DRAWINGS

FIG. 4 is an enlarged cross-sectional view of the battery carrying case of FIG. 1 taken along lines 4—4;

FIG. 5 is a view of FIG. 4 taken along lines 5-5 illustrating a slide means for supporting the battery carrying case;

FIG. 6 is a view of the battery carrying case of FIG. 4 taken along lines 6—6; and FIG. 7 is a cross-sectional view of FIG. 6 taken along lines 7—7.

DESCRIPTION OF THE PREFERRED EMBODIMENT

Figures 1, 2, 3:
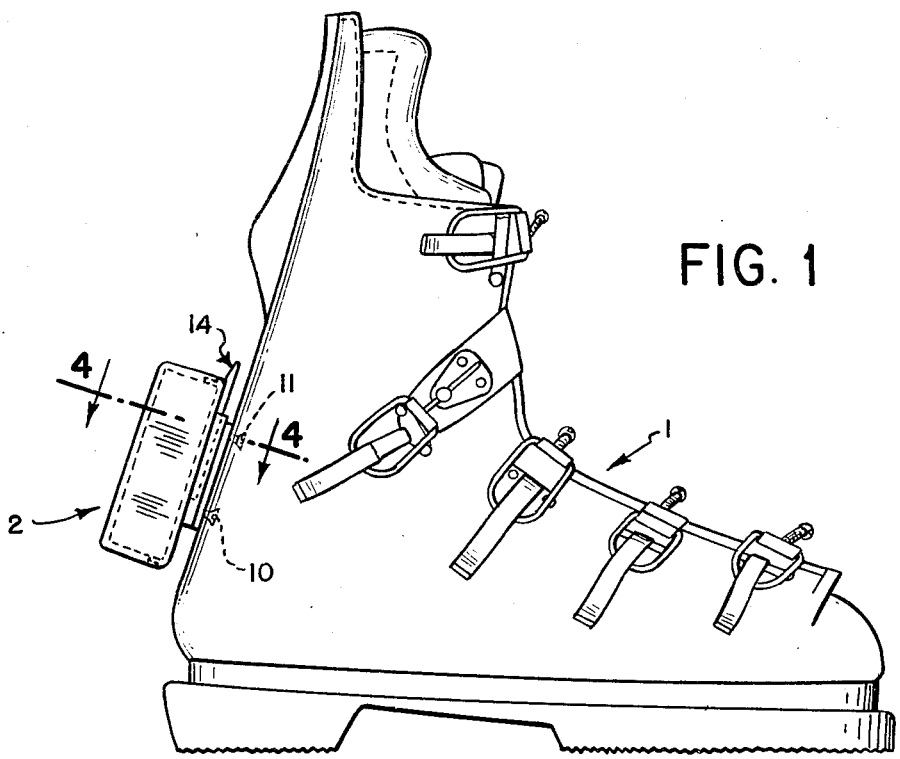
FIG. 1 is a side view of a ski boot showing the placement of a battery carrying case constructed according to the invention.
FIG. 2 is a partial sectional plane view of an inner sole for use in the boot of FIG. 1.
FIG. 3 is an enlarged cross-sectional view of FIG. 2 taken along lines 3—3.

Referring to FIG. 1, there is illustrated a conventional ski boot 1 having thereon a combined battery carrying case and switch 2 where a battery in the case provides energy for a heated inner sole 3 adapted to be contained in the boot. The inner sole 3 comprises a layer of high density cellular polyurethane foam material 4 having a pressure sensitive adhesive 5 on one side thereof. The other side of the layer of foam material has a layer of fabric material 6 applied thereto where the material preferably comprises a plastic or a mixture of plastic and cotton. The fabric layer 6 is held to the foam material by pressure sensitive adhesive 7. Electrical resistance elements 8 are interposed between the foam material 4 and the fabric material 6 and connect with a lead wire 9.

As shown in FIG. 2, the elements 8 are disposed in the toe area of the inner sole and are so arranged that there is a greater concentration of the elements towards the foreward end of the inner sole to provide more heat in the toe area. It has been found that in cold weather situations, the portion of a foot most sensitive to cold is the toe portion rather than other portions such as the heel.

The lead wire 9 may extend along the bottom of the boot to the rear thereof to connect with clamping screws 10 and 10' which extending through the boot and are threaded into metallic brackets 12 and 12'. In some boots, or example ski boots having a double wall construction comprising inner and outer boots, the wire 9 may extend out through the tongue area of the inner boot and around the inner boot to the heel area of the outer boot to connect with the clamping screws.

As shown in FIGS. 4–7 the metallic brackets 12 and 12' have a non-metallic slide 14 attached to the brackets by means of screws 15—15' and 16—16'. The slide 14 has a tongue portion 18 which is movable in the direction of the double ended arrow 20 as shown in FIG. 7. The tongue 12 has a ledge 22 thereon which acts as a locking latch described in greater detail hereafter.

Referring to FIG. 4, there is illustrated the battery carrying case 2 which carries therein a battery 24. The case 2 has a plastic container 26 which is adapted to be closed by a plastic cover 28. The cover has a reduced shoulder portion 30 which snaps into the outer shoulder portion 32 of the container whereby the cover may be secured to the container.

The cover 28 has rails 34 and 34' thereon to form a track which may slidably engage the slide 14.

Cooper strips 36 and 36' are contained within cutouts on the cover 28 and are held in the cutouts by means of rivets 38 and 38'. Each strip has a raised contact or shoulder portion 40 and 40' adapted to engage screws 15 and 15' where the screws likewise act as contacts. Conventional wiring, not shown, extends from the poles of the battery 24 to the rivets 38 and 38'. When the case 2 is in the position shown in FIG. 7, a contact will be made between the raised portion 40 and the screw 15 to complete one leg of an electrical circuit between the battery and the heating elements 8 by way of the rivet 38, contact 40, contact 15 of the slide, through the metallic bracket 12, screw 10 and to the lead wire 9. Similar contact is made through the similarly numbered elements to complete the circuit back to the battery.

The cover 28 has a first indentation 42 and a second indentation 44 adapted to engage the shoulder 22 on the tongue 18 to lock the case against movement relative to the slide. In FIG. 7 the shoulder 22 is shown engaging the first indentation 42 and latching or locking the battery case in the first or on position.

The cover 28 further has a cutout portion 46 which acts in connection with the tapered portion 50 of the tongue 18 as a guide and cam to assist in positioning the rails 34 to engage the slide 14. Stops 48 and 48' are included at the end of the rails 34 and 34' and limit the downward movement of the case on the slide.

Preferably the battery 24 is of the rechargable type. In the construction shown, the battery may be easily removed from the track and applied to a recharger.

The operation of the device is as follows. The tongue is moved towards the boot and the battery case is applied to the slide 14. The tapered portion 50 will engage the cam 46 to assist in directing the rails of the case into engagement with the slide as the case is slid down onto the slide. The tongue 18 is then released. As the case is moved down the slide, the shoulder 22 will engage the indentation 44 thus latching or locking the case into its off or second position. As shown in FIG. 7, the tongue has on the end thereof "on" and "off" notations. When the latch engages the indentation 44, only the "off" notation will show above the case. When it is desired to warm a foot, the tongue 18 is again moved to the right as shown in FIG. 7 allowing the case to be moved down the slide until the shoulder 22 engages the indentation 42 where the tongue is allowed to return to its position as shown in FIG. 7. At this position the contacts 40 and 40' on the copper strips engage the contacts 15 and 15' on the slide thus completing an electrical circuit with the inner sole.

An inner sole and battery case construction according to my invention may be easily applied to conventional boots. All that is required is to drill four small holes in the heel area of the boot so as to receive the screws 10—10' and 11—11' by which the metallic brackets 12 and 12' are held to the boot and the electrical connection between the interior and exterior of the boot is made. The inner sole may be conveniently cut to fit in the boot. The use of a pressure sensitive adhesive allows easy placement of the inner sole in the boot as all that is required is to place the inner sole in the boot, put the boot on, and step on it whereby the weight of the wearer will then assure sufficient pressure to make the inner sole stick to the boot. For packaging purposes, the pressure sensitive adhesive would have a slip paper protective covering overlying the adhesive which would be stripped off prior to use.

I claim:

1. An electrically heated inner sole adapted to be applied to the interior of a boot, comprising a layer of cellular polyurethane foam material, a pressure sensitive adhesive on one side of said layer of foam material, a layer of fabric material on the other side of said layer of foam material opposite said pressure sensitive adhesive, heating elements positioned between said layer of foam material and said layer of fabric material and an electrical lead connected to said heating elements and extending exteriorly of said inner sole adapted to be connected to a source of energy.

2. An electrically heated inner sole according to claim 1 wherein the portion of the inner sole adapted to be positioned in the toe area of the boot has a greater concentration of heating elements positioned between said layer of foam material and said layer of fabric material than the remainder of the inner sole.

3. An electrically heated inner sole adpated to be applied to the interior of a boot, said inner sole comprising a layer of insulating material substantially conforming in shape to the bottom of a boot with said inner sole having a toe area, heating elements overlying said toe area with the remainder of said layer of insulating material being free of heating elements, a lining layer overlying said heating elements and said layer of insulating material, a layer of pressure sensitive adhesive underlying said insulating layer whereby said inner sole may be affixed in a boot, and electrical leads connected to said heating elements and extending exteriorly of said inner sole adapted to be connected to a source of energy.

* * * * *

UNITED STATES PATENT AND TRADEMARK OFFICE
CERTIFICATE OF CORRECTION

PATENT NO. : 3,946,193
DATED : March 23, 1976
INVENTOR(S) : ERIK O. GIESE

It is certified that error appears in the above-identified patent and that said Letters Patent are hereby corrected as shown below:

After item [76] insert item [73] Assignee: Comfort Products, Inc., Aspen, Colorado Signed and Sealed this Tenth Day of August 1976

[SEAL]

Attest:

RUTH C. MASON
Attesting Officer

C. MARSHALL DANN
Commissioner of Patents and Trademarks